(12) United States Patent
Justis et al.

(10) Patent No.: US 7,803,188 B2
(45) Date of Patent: Sep. 28, 2010

(54) SYSTEMS AND METHODS FOR INTRAVERTEBRAL REDUCTION

(75) Inventors: Jeff R. Justis, Collierville, TN (US); Michael C. Sherman, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 10/648,056

(22) Filed: Aug. 26, 2003

(65) Prior Publication Data

US 2004/0097930 A1     May 20, 2004

Related U.S. Application Data

(60) Provisional application No. 60/406,362, filed on Aug. 27, 2002.

(51) Int. Cl.
    *A61F 2/44* (2006.01)
(52) U.S. Cl. .................................. 623/17.11
(58) Field of Classification Search ... 623/17.11–17.16; 606/90–94, 232
    See application file for complete search history.

(56) References Cited

U.S. PATENT DOCUMENTS

| | | | |
|---|---|---|---|
| 4,969,888 A | 11/1990 | Scholten et al. | |
| 5,108,404 A | 4/1992 | Scholten et al. | |
| 5,171,280 A | 12/1992 | Baumgartner | |
| 5,370,661 A * | 12/1994 | Branch | 606/232 |
| 5,514,153 A | 5/1996 | Bonutti | |
| 5,534,023 A * | 7/1996 | Henley | 623/8 |
| 5,549,679 A * | 8/1996 | Kuslich | 623/17.12 |
| 5,755,797 A * | 5/1998 | Baumgartner | 623/17.16 |
| 5,878,886 A * | 3/1999 | Marshall | 206/470 |
| 5,961,554 A | 10/1999 | Janson et al. | |
| 5,972,015 A | 10/1999 | Scribner et al. | |
| 6,066,154 A | 5/2000 | Reiley et al. | |
| 6,179,873 B1 | 1/2001 | Zientek | |
| 6,231,615 B1 * | 5/2001 | Preissman | 623/23.73 |
| 6,235,043 B1 | 5/2001 | Reiley et al. | |
| 6,248,110 B1 | 6/2001 | Reiley et al. | |
| 6,280,456 B1 | 8/2001 | Scribner et al. | |
| 6,387,130 B1 * | 5/2002 | Stone et al. | 623/17.16 |
| 6,423,083 B2 | 7/2002 | Reiley et al. | |
| 6,595,998 B2 | 7/2003 | Johnson et al. | |
| 6,620,196 B1 * | 9/2003 | Trieu | 623/17.16 |
| 6,632,235 B2 * | 10/2003 | Weikel et al. | 606/192 |

(Continued)

FOREIGN PATENT DOCUMENTS

EP     0 621 020 A1     10/1994

(Continued)

OTHER PUBLICATIONS

International Search Report in PCT/US2003/026615, mailed May 5, 2004, 6 pages.

*Primary Examiner*—Alvin Stewart
(74) *Attorney, Agent, or Firm*—Haynes and Boone, LLP

(57) ABSTRACT

Intravertebral reduction systems are provided to restore a deformed or damaged vertebral body to a desired configuration. The reduction systems can include a plurality of reduction elements sequentially positionable in the intravertebral space for reduction of the same. The reduction systems can also include reduction elements that include a linear insertion configuration and are deformable transversely to the linear insertion configuration in the intravertebral space.

37 Claims, 4 Drawing Sheets

U.S. PATENT DOCUMENTS

| | | | |
|---|---|---|---|
| 6,740,093 B2 * | 5/2004 | Hochschuler et al. | 606/94 |
| 7,025,771 B2 * | 4/2006 | Kuslich et al. | 606/93 |
| 7,153,305 B2 * | 12/2006 | Johnson et al. | 606/90 |
| 7,311,713 B2 * | 12/2007 | Johnson et al. | 606/90 |
| 7,351,262 B2 * | 4/2008 | Bindseil et al. | 623/17.16 |
| 7,465,318 B2 * | 12/2008 | Sennett et al. | 623/17.12 |
| 7,621,950 B1 * | 11/2009 | Globerman et al. | 623/17.11 |
| 2002/0068974 A1 | 6/2002 | Kuslich et al. | |
| 2002/0077701 A1 * | 6/2002 | Kuslich | 623/17.12 |
| 2003/0130664 A1 | 7/2003 | Boucher et al. | |
| 2003/0171812 A1 | 9/2003 | Grunberg et al. | |
| 2004/0167532 A1 * | 8/2004 | Olson et al. | 606/93 |
| 2004/0215343 A1 * | 10/2004 | Hochschuler et al. | 623/17.12 |
| 2004/0249464 A1 * | 12/2004 | Bindseil et al. | 623/17.16 |
| 2005/0015148 A1 * | 1/2005 | Jansen et al. | 623/17.11 |
| 2005/0278023 A1 * | 12/2005 | Zwirkoski | 623/11.11 |
| 2006/0004455 A1 * | 1/2006 | Leonard et al. | 623/17.15 |
| 2006/0052874 A1 * | 3/2006 | Johnson et al. | 623/17.16 |
| 2006/0085081 A1 * | 4/2006 | Shadduck et al. | 623/23.76 |
| 2006/0100304 A1 * | 5/2006 | Vresilovic et al. | 523/113 |
| 2006/0106461 A1 * | 5/2006 | Embry et al. | 623/17.12 |
| 2006/0184246 A1 * | 8/2006 | Zwirkoski | 623/11.11 |
| 2006/0265077 A1 * | 11/2006 | Zwirkoski | 623/17.16 |
| 2007/0055274 A1 * | 3/2007 | Appenzeller et al. | 606/90 |
| 2007/0088436 A1 * | 4/2007 | Parsons et al. | 623/17.11 |
| 2007/0093822 A1 * | 4/2007 | Dutoit et al. | 606/61 |
| 2007/0093899 A1 * | 4/2007 | Dutoit et al. | 623/17.11 |
| 2007/0093912 A1 * | 4/2007 | Borden | 623/23.75 |
| 2007/0162044 A1 * | 7/2007 | Marino | 606/96 |
| 2007/0162132 A1 * | 7/2007 | Messerli | 623/17.11 |
| 2007/0173939 A1 * | 7/2007 | Kim et al. | 623/17.11 |
| 2007/0179612 A1 * | 8/2007 | Johnson et al. | 623/17.11 |
| 2007/0233146 A1 * | 10/2007 | Henniges et al. | 606/91 |
| 2008/0009792 A1 * | 1/2008 | Henniges et al. | 604/98.01 |
| 2008/0039586 A1 * | 2/2008 | Hasenwinkel et al. | 525/192 |
| 2008/0051800 A1 * | 2/2008 | Diaz et al. | 606/92 |
| 2008/0133012 A1 * | 6/2008 | McGuckin | 623/17.12 |
| 2009/0030468 A1 * | 1/2009 | Sennett et al. | 606/86 R |
| 2009/0112221 A1 * | 4/2009 | Burke et al. | 606/102 |
| 2009/0164016 A1 * | 6/2009 | Georgy et al. | 623/17.11 |
| 2009/0177206 A1 * | 7/2009 | Lozier et al. | 606/93 |
| 2009/0182427 A1 * | 7/2009 | Liu et al. | 623/16.11 |
| 2009/0187190 A1 * | 7/2009 | Johnson et al. | 606/79 |
| 2009/0187249 A1 * | 7/2009 | Osman | 623/17.16 |
| 2009/0204216 A1 * | 8/2009 | Biedermann et al. | 623/17.12 |
| 2009/0234361 A9 * | 9/2009 | Johnson et al. | 606/90 |
| 2009/0240334 A1 * | 9/2009 | Richelsoph | 623/17.16 |
| 2009/0264942 A1 * | 10/2009 | Beyar et al. | 606/86 R |
| 2009/0270902 A1 * | 10/2009 | Assell et al. | 606/191 |
| 2009/0275995 A1 * | 11/2009 | Truckai et al. | 606/86 R |

FOREIGN PATENT DOCUMENTS

| | | |
|---|---|---|
| WO | WO 02/30338 A1 | 4/2002 |
| WO | WO 02/43628 A1 | 6/2002 |
| WO | WO 02/47563 A1 | 6/2002 |
| WO | 02/071921 A2 | 9/2002 |
| WO | WO 02/071821 A2 | 9/2002 |
| WO | WO 03/007854 A1 | 1/2003 |
| WO | WO 03/059180 A2 | 7/2003 |

* cited by examiner

US 7,803,188 B2

SYSTEMS AND METHODS FOR INTRAVERTEBRAL REDUCTION

CROSS-REFERENCE TO RELATED APPLICATION

This application claims the benefit of the filing date of Provisional Application Ser. No. 60/406,362 filed on Aug. 27, 2002, which is hereby incorporated by reference in its entirety.

BACKGROUND

Various instruments and methods for the treatment of compression-type bone fractures and other osteoporotic and/or non-osteoporotic conditions have been developed. Such methods generally include a series of steps performed by a surgeon to correct and stabilize the compression fracture. A cavity is typically formed in the bone to be treated, followed by the insertion of an inflatable balloon-like device into the bone cavity. Inflation of the balloon-like device causes compaction of the cancellous bone about the balloon and/or bone marrow against the inner cortical wall of the bone, thereby resulting in enlargement of the bone cavity and/or reduction of the compression fracture. The balloon-like device is then deflated and removed from the bone cavity. A biocompatible filling material, such as methylmethacrylate cement or a synthetic bone substitute, is sometimes delivered into the bone cavity and allowed to set to a hardened condition to provide internal structural support to the bone.

Expansion and subsequent removal of the balloon-like device can leave a large void in the intravertebral space. Creation of a void in the intravertebral space results in filler material being required to support the vertebra. Also, balloon-like devices require exertion of pressure for expansion of the balloon and/or insertion of material into the balloon or the space created by expansion of the balloon. The pressurized working environment may result in over-compaction of the cancellous bone and in material placed in the intravertebral space entering the spinal canal and/or venous structures associated with the spinal column.

Thus, there is a need for surgical instrumentation and methods for use in treatment of vertebral fractures and other deformities that can more beneficially be employed to compact cancellous bone and support spinal column loads post-reduction.

SUMMARY

There is provided at least one reduction element positionable in the intravertebral space in contact with bony tissue of the vertebra that simultaneously compacts the bony tissue and occupies the volume created by compaction of the bony tissue in a non-pressurized, non-fluid environment to exert an outwardly directed corrective force to the vertebra.

According to one aspect, an intravertebral reduction system comprises a plurality of reduction elements positionable adjacent one another in an intravertebral space in contact with bony tissue. The plurality of reduction elements act randomly one upon the other upon sequential positioning thereof in the intravertebral space to compress cancellous bony tissue and apply an outwardly directed corrective force in the intravertebral space to restore the vertebral body.

According to another aspect, an intravertebral reduction system comprises one or more elongate reduction elements positionable in an intravertebral space. The one or more elongate reduction elements each include a linear insertion configuration and are deformable transversely to the insertion configuration to substantially occupy a volume within the intravertebral space and compress cancellous bony tissue within the vertebral body. An outwardly directed corrective force is applied to the vertebral body as the one or more elongated elements are deformed in the intravertebral space.

According to another aspect, a vertebral fracture is reduced by accessing an intravertebral space of the vertebra; sequentially positioning a plurality of reduction elements in the intravertebral space in contact with bony tissue of the vertebra; and filling the vertebral space with a plurality of sequentially positioned reduction elements to substantially occupy the intravertebral space and exert an outwardly and radially directed corrective force to the vertebra.

According to one aspect, an intravertebral reduction system includes a plurality of reduction elements positionable in an intravertebral space that bear against one another and apply an outwardly directed force to restore the vertebral body. A material is placed around the reduction elements for post-operative maintenance and stability.

According to another aspect, an intravertebral reduction system includes a plurality of interconnected reduction elements positionable in an intravertebral space. With at least a portion of the intravertebral space occupied with the reduction elements, the plurality of reduction elements bear against one another and apply an outwardly directed corrective force from the intravertebral space to restore the vertebral body. The connecting element provides for removal of the reduction elements from the intravertebral space when it is restored.

According to another aspect, an intravertebral reduction system includes an elongated reduction element positionable in an intravertebral space. The elongated reduction element folds or gathers onto itself in the intravertebral space as it is positioned therein, and applies an outwardly directed corrective force to the vertebral bodies.

According to another aspect, an intravertebral reduction system includes one or more elongated reduction elements positionable in an intravertebral space that are coiled from their linear insertion configuration into the intravertebral space into contact with the vertebral body to apply an outwardly directed corrective force thereto as the one or more elongated elements are positioned into the intravertebral space.

These and other aspects will also be apparent from the following description.

DESCRIPTION OF THE ILLUSTRATED EMBODIMENTS

Figure 1:
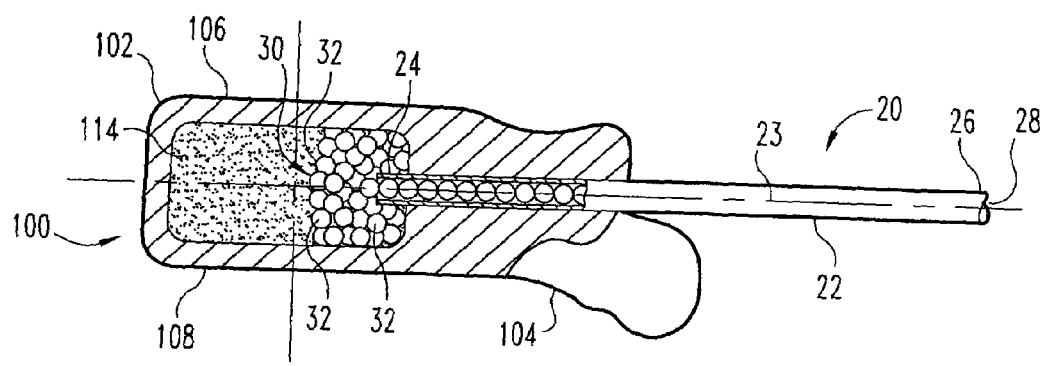
FIG. 1 is a side view of an intravertebral reduction system and vertebral body according to one embodiment.

For the purposes of promoting an understanding of the principles of the invention, reference will now be made to the embodiments illustrated in the drawings and specific language will be used to describe the same. It will nevertheless be understood that no limitation of the scope of the invention is hereby intended, such alterations and further modifications in the illustrated devices, and such further applications of the principles of the invention as illustrated herein being contemplated as would normally occur to one skilled in the art to which the invention relates.

Figure 2:
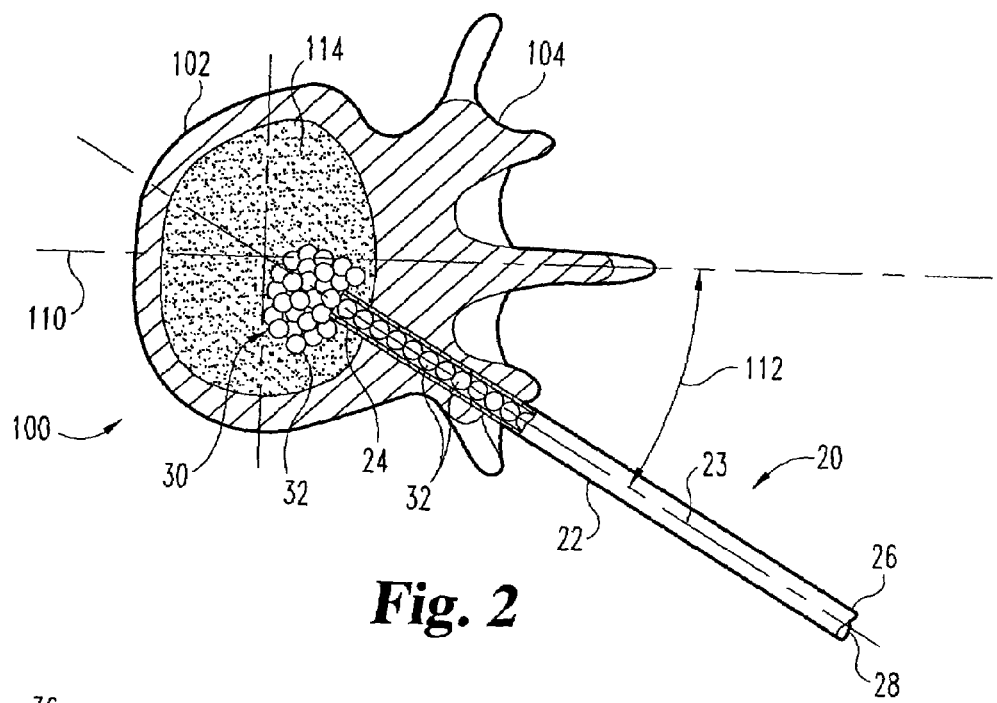
FIG. 2 is a plan view of the system of FIG. 1.

Referring to FIGS. 1 and 2, shown therein is a system 20 for treatment of the spine according to one embodiment. System 20 can be placed adjacent a spinal structure for intravertebral displacement or reduction of a spinal fracture or other deformity. It is contemplated that system 20 may be used in intra-body applications such as, for example, a vertebroplasty procedure to compact cancellous bone within the vertebral body and/or to reduce a compression fracture of the vertebral body. The system 20 includes one or more reduction elements to compress cancellous bony tissue as inserted and simultaneously occupy a volume created in the intravertebral space to achieve intravertebral reduction in a non-pressurized, non-fluid environment.

Other uses contemplate interbody applications such as, for example, to distract a space between adjacent vertebral bodies, such as the vertebral disc space. It is contemplated that the spinal structure may include a spinal implant such as, for example, a cage device, or any other structure used in association with treatment of the spine. Additionally, although system 20 is illustrated and described in the context of treatment of a human spine, it is contemplated that system 20 may be used to treat other animals. It is also contemplated that system 20 may be used in association with applications outside of the spinal field such as, for example, to treat other types of bony structures.

System 20 is comprised of a delivery member 22 extending generally along a longitudinal axis 23 and having a distal end portion 24 and a proximal end portion 26. Although the illustrated embodiment depicts delivery member 22 as having a generally linear, tubular configuration, it should be understood that delivery member 22 may take on other configurations as well, such as, for example, a curvilinear configuration, multiple curved and linear segments, two or more angled segments, a hinged configuration, and/or a bendable configuration. Delivery member 22 also includes a passage 28 extending therethrough between proximal end portion 26 and distal end portion 24. Delivery member 22 can be provided with an enclosed passage 28. Other embodiments contemplated that passage 28 can be open along all or a portion of the length of delivery member 22.

Delivery member 22 can be positioned adjacent the desired entry location on or near vertebral body 100 in a minimally invasive surgical procedure. Although not shown, it is further contemplated that viewing systems can be provided to view the intravertebral procedures. Contemplated viewing systems include, for example, endoscopic viewing systems positioned through delivery member 22 or through a second portal; microscopic viewing systems positioned over delivery member 22 or over another viewing portal; fluoroscopic and radiographic viewing systems, and surgical navigation systems. Furthermore, the reduction systems discussed herein can be employed in minimally invasive surgical procedures, and also in open surgical procedures in which skin and tissue are retracted to at least partially expose the spinal structure to be treated.

In FIGS. 1 and 2 there is shown therein vertebral body 100 having an anterior portion 102 and a posterior portion 104. Anterior portion 102 includes an upper endplate 106 and an opposite lower endplate 108. In the illustrated embodiment, delivery member 22 is positioned in a postero-lateral approach to the vertebral body along axis 23. Axis 23 forms an angle 112 with axis 110 lying in the sagittal plane of the spinal column. A postero-lateral approach, particularly in the lumbar region of spine, minimizes disruption to the anatomy surrounding the spinal column and the insertion depth required to access the vertebral body. It should be understood, however, that other approaches are also contemplated, including anterior, antero-lateral, lateral and posterior approaches to the spinal column. It is further contemplated that multiple approaches with more than one delivery member 22 can be employed.

A reduction system 30 is positionable through or deliverable through delivery member 22 and into a confined volume within the intravertebral space of vertebra 100 to reduce, displace and/or stabilize a fracture or deformed segment of bone of anterior portion 102 of vertebral body 100. In FIGS. 1 and 2, reduction system 30 comprises a plurality of discrete reduction elements 32 introduced into the intravertebral space 114 through delivery member 22. Reduction elements 32 can be introduced sequentially, individually or in small numbers into intravertebral space 114 to create an intravertebral distraction force to restore the height of vertebral body 100 between endplates 106, 108 as reduction elements 32 fill at least a portion of intravertebral space 114.

As shown in FIG. 1, it is contemplated that reduction system 30 can occupy a height in its post-operative configuration in vertebral body 100 sufficient to extend between endplates 106, 108 to restore the vertebral body height or shape therebetween. Furthermore, removal of cancellous bone material in vertebral body 100 is not necessary to accommodate reduction elements 32, although removal of all or a portion of the cancellous bone material is not precluded. The placement of reduction elements 32 in the confined volume of intravertebral space 114 compresses the cancellous bone material resulting in outwardly directed pressure or forces on the cortical bone of anterior portion 102 of vertebral body 100. The outwardly directed pressure or forces restore vertebral body 100 to a desired height and width between endplates 106, 108, reducing vertebral fractures or other deformities.

In the illustrated embodiment of FIG. 1, reduction elements 32 include a generally spherical shape and sufficient rigidity to push randomly and radially against one another to compress cancellous bony tissue as reduction elements 32 are forced into the confined volume of intravertebral space 114 through delivery member 22. When the desired reduction has been obtained through introduction of an appropriate number of reduction elements 32, the reduction elements 32 can be fixed in the intravertebral space with additional material to post-operatively maintain the vertebral reduction obtained. For example, a resorbable bone cement, poly(methyl methacrylate) (PMMA), or suitable flowable, curable material can be placed intravertebrally and into the voids between the reduction elements 32 to fix the reduction elements 32 in position. Moreover, the material can comprise an effective amount of a bone morphogenetic protein, transforming growth factor β1, insulin-like growth factor 1, platelet-derived growth factor, fibroblast growth factor, LIM mineralization protein (LMP), and combinations thereof or other therapeutic or infection resistant agent, held within a suitable carrier material.

Figure 3:
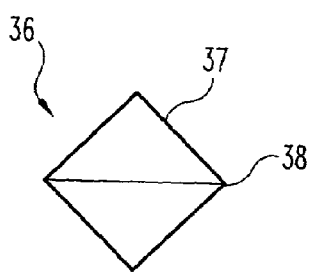
FIG. 3 is an elevation view of one embodiment reduction element.
Figure 4:
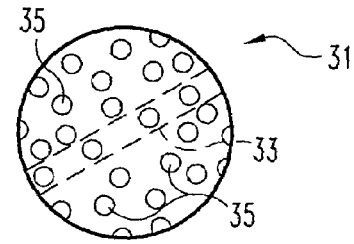
FIG. 4 is an elevation view of another embodiment reduction element.

It is further contemplated that reduction elements 32 could be provided with a non-spherical geometry that facilitates interlocking between adjacent reduction elements, such as shown with reduction element 36 in FIG. 3. For example, reduction element 36 includes planar exterior wall portions 37, and can also include jagged, barbed or otherwise non-uniform exterior surface features 38, or other regular or irregular shape that promotes interlocking or frictional engagement of adjacent reduction elements and of the reduction elements with the adjacent bone tissue. It is further contemplated that reduction elements include surface features to receive and interlock with the material positioned in intravertebral space 114 and/or bony tissue. For example, reduction element 31 in FIG. 4 includes recesses 35 in the outer surface thereof. Cavities or chambers 33 could extend between outer surfaces of the reduction element to receive material and/or bone growth therethrough, further facilitating post-operative maintenance of the positioning of the reduction elements in the intravertebral space 114.

It is contemplated that reduction elements 32 can be made from any biocompatible material providing sufficient distraction forces when positioned into and occupying the intravertebral space. Examples of suitable materials for reduction elements 32 include metallic material and non-metallic materials. Examples of metallic material include stainless steel and stainless steel alloys, titanium and titanium alloys, shape-memory alloys, cobalt chrome alloys. Examples of non-metallic, non-resorbable materials include polyetheretherketone (PEEK) and PEEK composites, non-reinforced polymers, carbon-reinforced polymer composites, carbon fiber, PMMA, resorbable polymers, calcium hydroxide, ceramics and combinations thereof and others as well. Examples of resorbable materials include polylactide, polyglycolide, tyrosine-derived polycarbonate, polyanhydride, polyorthoester, polyphosphazene, calcium phosphate, calcium hydroxide, hydroxyapatite, bioactive glass, and combinations thereof. Examples of tissue materials suitable for reduction elements 32 include hard tissues, connective tissues, demineralized bone matrix and combinations thereof.

Figure 5:
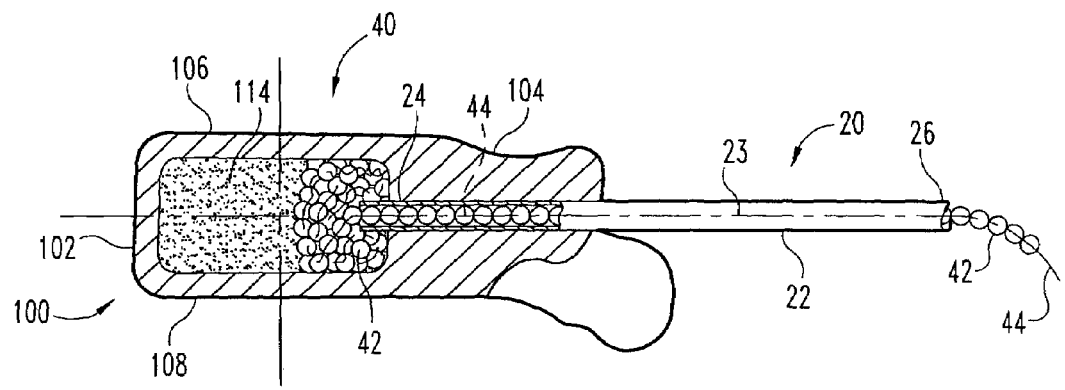
FIG. 5 is a side view of an intravertebral reduction system and vertebral body according to another embodiment.
Figure 6:
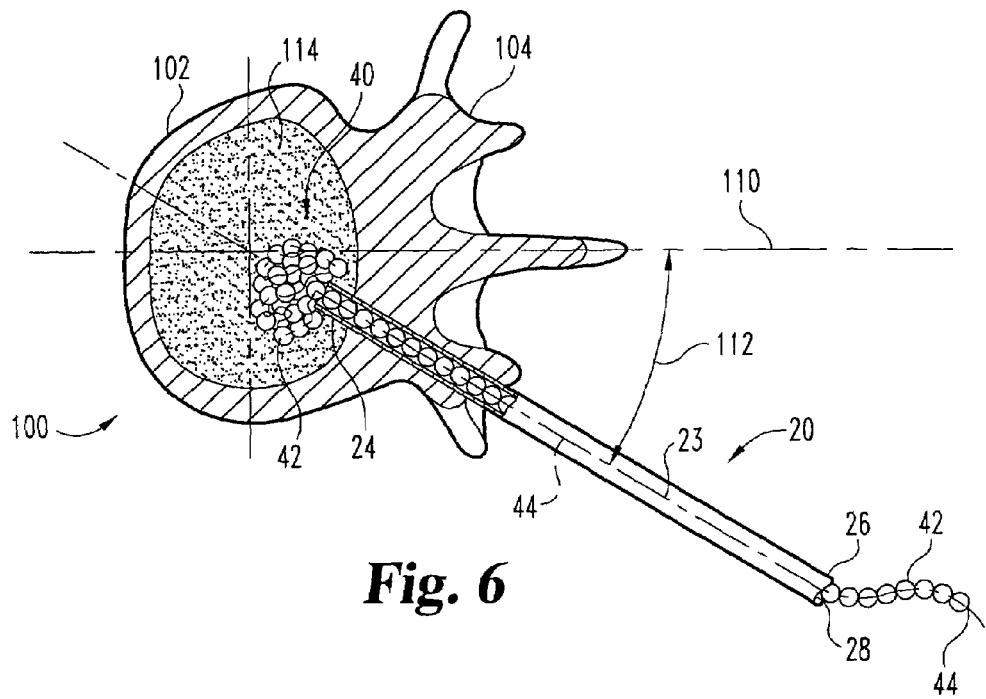
FIG. 6 is a plan view of the system of FIG. 5.

Referring now to FIGS. 5 and 6, another embodiment reduction system 40 is shown with reduction elements 42. Reduction elements 42 can have any form as discussed above with respect to reduction elements 32. However, reduction elements 42 are interconnected with connecting element 44. Connecting element 44 facilitates removal of some or all of reduction elements 42 from the intravertebral space 114 after reduction of vertebral body 100 has been obtained. As shown, reduction system 40 is positioned in intraverterbal space 114 to achieve the desired reduction. A proximal portion of reduction system 40 extends through delivery member 22 where it can be readily accessed to apply a removal force to remove the interconnected reduction elements 42 from intravertebral space 114.

With the reduction system 40 removed, material, such as the material discussed above with respect to reduction system 30, can be placed in the intravertebral space of the restored vertebral body to post-operatively maintain the desired intravertebral height and/or configuration. Other embodiments contemplate one or more other distraction maintenance devices could be positioned in the intravertebral space when all or a portion of reduction elements 42 are removed, such as a cage, strut, stent, or spacer device that extends toward endplates 104, 106.

In one embodiment, it is contemplated that connecting element 44 comprises one or more members in the form of a string, wire, cable, or the like having sufficient flexibility to fold and contort as reduction elements 42 are positioned in intravertebral space 114 of vertebral body 100 so that reduction elements 42 can be placed against one another. A pushing instrument or the like could be inserted through passage 28 of delivery member 22 alongside or behind reduction systems 30 or 40 to facilitate pushing of the reduction elements into intravertebral space 114.

In order to secure reduction elements 42 to connecting element 44, reduction elements 42 could be molded around connecting element 44. Also contemplated is threading or extending connecting element 44 through the body of each of or a subset of the reduction elements 42, or connecting element 44 could be threaded or extend through holes provided through each of or a subset of the reduction elements 42. It is also contemplated that individual connecting elements 44 could be employed between and connected to adjacent ones of the reduction elements 42.

In another embodiment, it is contemplated that reduction elements 42 remain in intravertebral space 114 post-operatively. The portion of system 40 outside intravertebral space 114 can be severed from the portion of system 40 in intravertebral space 114 when the desired reduction and/or distraction is obtained. A material, such as discussed above with respect to reduction system 30, can then be placed into the restored intravertebral space 114 through delivery member 22 for post-operative maintenance of the same.

Figure 7:
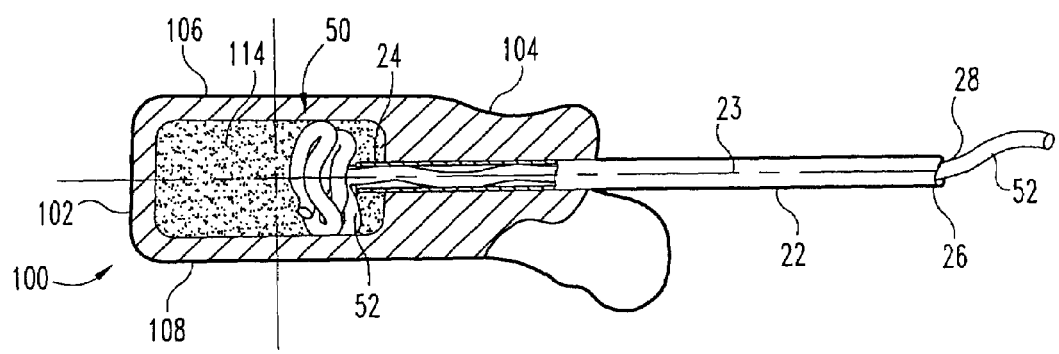
FIG. 7 is a side view of an intravertebral reduction system and vertebral body according to another embodiment.
Figure 8:
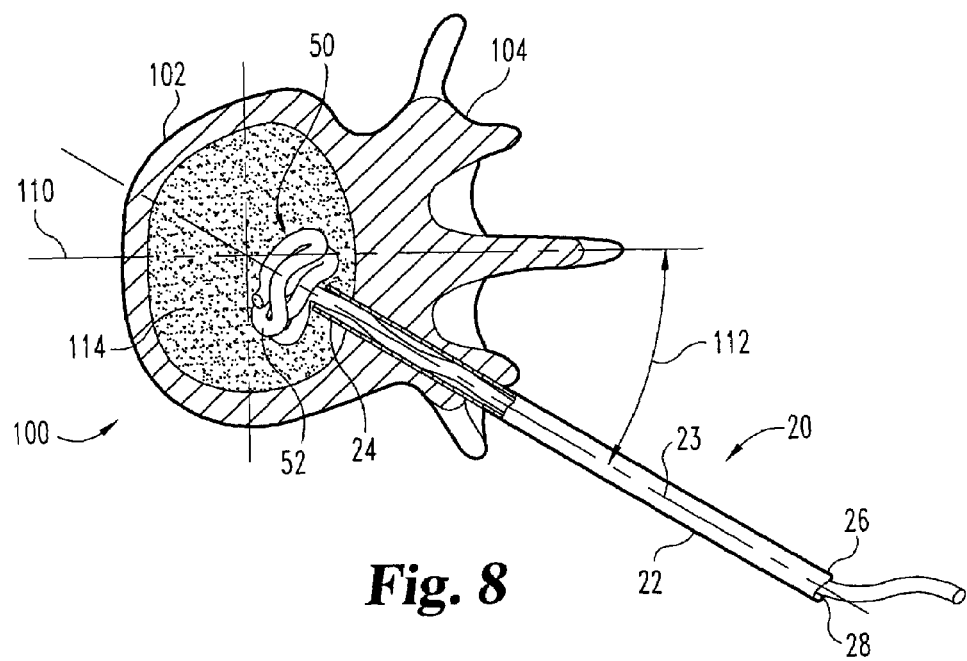
FIG. 8 is a plan view of the system of FIG. 7.

Referring now to FIGS. 7 and 8, another embodiment reduction system 50 is shown with reduction element 52. Reduction element 52 can include a semi-rigid wire, cable, strand, string, bar or other elongated form positionable through passage 28 of delivery member 22. Delivery member 22 can assist in maintaining or restrain reduction element 52 in a linear insertion configuration as it is delivered to intravertebral space 114. As reduction element 52 is positioned in intravertebral space 114, the reduction element 52 can fold back and forth to collapse onto itself in an accordion-like manner, distracting and/or reducing vertebral body 100 as it fills intravertebral space 114. Reduction element 52 thus moves from a linear insertion configuration to a reduction configuration in which reduction element 52 extends transversely to its linear insertion configuration and more axially along the central spinal column axis. Reduction element 52 substantially occupies the volume of intravertebral space created upon compression of the cancellous bony tissue.

When the desired distraction has been obtained, reduction element 52 can be severed at the intravertebral space to remain therein for maintaining the distracted intravertebral space. As discussed above with respect to reduction system 30, material can be delivered to the intravertebral space to occupy the volume of the intravertebral space around reduction element 52 and to stabilize its positioning in intravertebral space 114. In another embodiment, reduction element 52 is withdrawn from intravertebral space 114 after obtaining the desired distraction and/or reduction, and material and/or a distraction spacer is placed into the void created in the intravertebral space after removal of reduction element 52 to post-operatively maintain intravertebral space 114.

Figure 9:
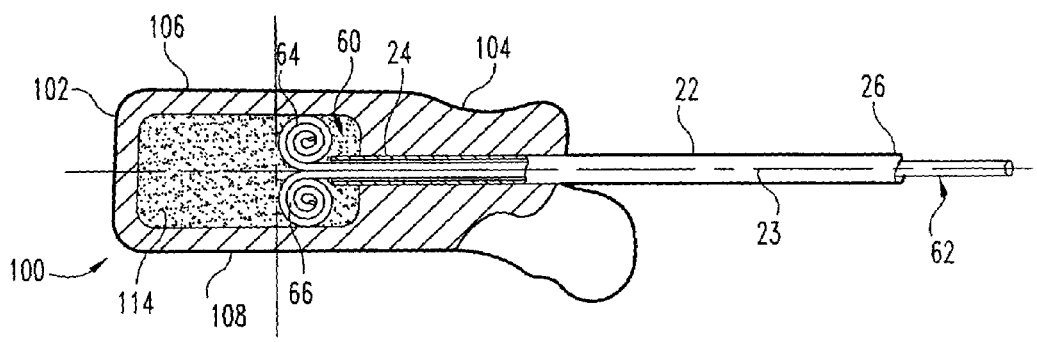
FIG. 9 is a side view of an intravertebral reduction system and vertebral body according to another embodiment.
Figure 10:
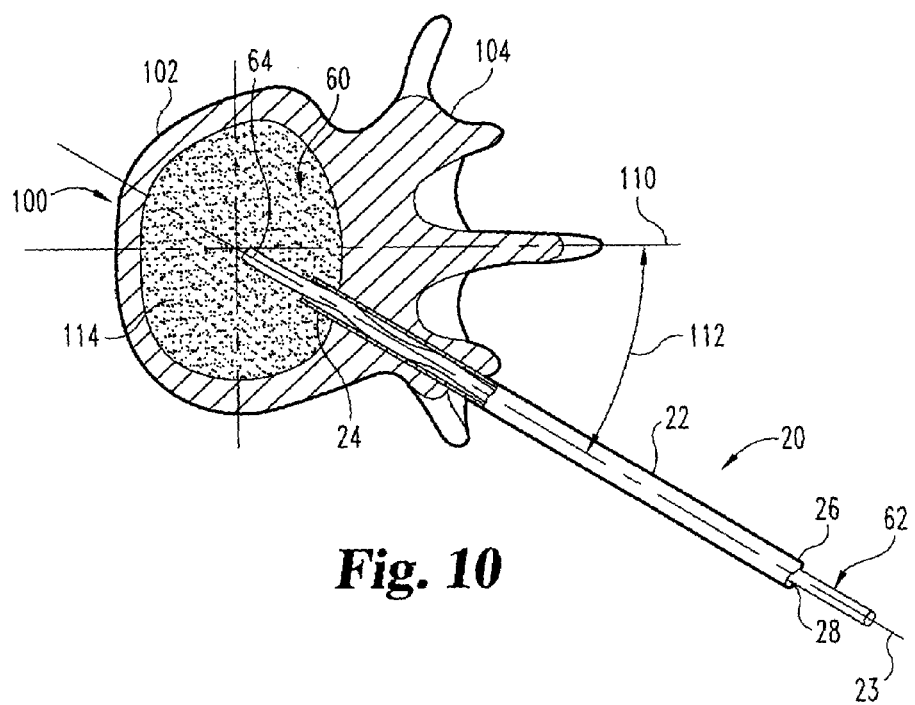
FIG. 10 is a plan view of the system of FIG. 9.

Referring now to FIGS. 9 and 10, another embodiment reduction system 60 is shown with reduction device 62. Reduction device 62 can include one or more semi-rigid wires, cables, strands, strings, bars or other elongate member positionable through passage 28 of delivery member 22. As the distal end of reduction device 62 is positioned in intravertebral space 114, reduction elements 64, 66 at the distal end of reduction device 62 can assume a configuration that extends into the intravertebral space 114 to provide an outwardly directed corrective force or pressure to vertebral body 100. For example, in the illustrated embodiment, reduction elements 64, 66 coil toward respective ones of the endplates 106, 108 as reduction elements 64, 66 are pushed positioned into intervertebral space 114. As the respective coils enlarge, an outwardly directed force or pressure is supplied to restore intravertebral space 114. Reduction elements 64, 66 thus move from a linear insertion configuration to a reduction configuration in which reduction elements 64, 66 extend axially along the central spinal column axis. Delivery member 22 can assist in maintaining or restraining reduction device 62 in a linear insertion configuration as it is delivered to intravertebral space 114.

When the desired distraction and/or reduction has been obtained, reduction device 62 can be severed at the intravertebral space so that reduction elements 64, 66 remain therein for maintaining the distracted intravertebral space. Reduction device 62 can remain in the intravertebral space to substantially occupy the volume of intravertebral space created upon compression of the cancellous bony tissue. As discussed above with respect to reduction system 30, material can be delivered to the intravertebral space to occupy the volume around reduction elements 64, 66 to stabilize their positioning in intravertebral space 114. In another embodiment, reduction elements 64, 66 are withdrawn from intravertebral space 114 after restoring vertebral body 100, and material and/or a distraction spacer or other device can be placed into the remaining intravertebral space after removal of reduction elements 64, 66 to post-operatively maintain intravertebral space 114.

In one embodiment, it is contemplated that reduction element 52 and/or reduction elements 64, 66 can be are made from shape memory alloy material (SMA). More specifically, SMAs are known to exhibit a characteristic or behavior in which a particular component formed of an SMA is capable of being deformed from an initial "memorized" shape or configuration to a different shape or configuration, and then reformed back toward its initial shape or configuration.

Other embodiments contemplate that reduction elements 52 and/or reduction elements 64, 66 could be made from a semi-rigid elastomer, spring metal, or other suitable material capable of assuming the contemplated configuration for insertion in a low profile arrangement and thereafter expanding, folding, coiling or otherwise generally conforming to the intravertebral space 114 to provide an outwardly directed corrective force to vertebral body 100. The reduction elements, when positioned in the intravertebral space, provide support of the intravertebral space and can also exert outward forces to reduce vertebral fractures or to treat other conditions. As inserted, the reduction elements compress cancellous bony tissue and simultaneously occupy a volume created in the intravertebral space to achieve intravertebral reduction in a non-pressurized, non-fluid environment. The reduction elements can be fixed in place with a suitable flowable material that occupies voids between the reduction elements and maintains intravertebral stabilization. Material can also be placed in the intravertebral space to maintain reduction achieved by removed reduction elements. With reduction achieved prior to its placement, the flowable material need not be injected under pressure or in significant quantities, reducing the potential for the material to enter the spinal canal or venous structures.

While the invention has been illustrated and described in detail in the drawings and foregoing description, the same is to be considered as illustrative and not restrictive in character. All changes and modifications that come within the spirit of the invention are desired to be protected.

What is claimed is:

1. An intravertebral reduction system, comprising:
 a plurality of reduction elements positionable in an intravertebral space adjacent one another in contact with bony tissue, wherein said plurality of reduction elements act one upon the other upon sequential positioning thereof in the intravertebral space to compress cancellous bony tissue and apply an outwardly directed corrective force in the vertebral body, wherein said plurality of reduction elements are selected in number to occupy a reduction element volume within the intravertebral space that obtains a desired vertebral reduction;
 voids between respective ones of said plurality of reduction elements; and
 means for fixing said plurality of reduction elements at said reduction element volume in engagement with one another in the intravertebral space in a manner maintaining the obtained vertebral reduction despite variations in spinal loading, said means including material filling said voids and locking said plurality of reduction elements relative to one another.

2. The system of claim 1, wherein said plurality of reduction elements are linked to one another.

3. The system of claim 2, wherein said plurality of reduction elements are linked by a connecting element extending through said plurality of reduction elements.

4. The system of claim 2, wherein said plurality of reduction elements are linked by a connecting element extending between adjacent ones of said plurality of reduction elements.

5. The system of claim 1, wherein said plurality of reduction elements each include a spherical shape.

6. The system of claim 1, wherein said plurality of reduction elements are comprised of a material selected from the group consisting of: PMMA, resorbable polymers, and calcium hydroxide.

7. The system of claim 1, wherein at least a portion of said plurality of reduction elements include exterior surface features to facilitate engagement between adjacent reduction elements.

8. The system of claim 7, wherein said exterior surface features include planar surfaces.

9. The system of claim 7, wherein said exterior surface features include recesses.

10. The system of claim 9, wherein said material is placeable in the intravertebral space around said plurality of reduction elements and in said recesses thereof for post-operative maintenance and stability of said plurality of reduction elements in the intravertebral space.

11. The system of claim 7, wherein said exterior surface features include a cavity extending through said reduction element.

12. The system of claim 1, wherein said material is placeable in the intravertebral space around said plurality of reduction elements for post-operative maintenance and stability of said plurality of reduction elements in the intravertebral space.

13. The system of claim 12, wherein said material is selected from the group consisting of: PMMA and resorbable bone cement.

14. The system of claim 1, further comprising a delivery member positionable adjacent the intravertebral space, said delivery member including a passage for delivery of said plurality of reduction elements thereto.

15. The system of claim 1, wherein said plurality of reduction elements are selected to occupy sufficient intravertebral space to restore a height of the vertebral body between endplates thereof.

16. An intravertebral reduction system, comprising:
a plurality of reduction elements positionable in an intravertebral space adjacent one another in contact with bony tissue, wherein said plurality of reduction elements act randomly and radially one upon the other upon sequential positioning thereof in the intravertebral space compressing cancellous bony tissue and applying an outwardly directed corrective force in the vertebral body, wherein said plurality of reduction elements are selected in number to occupy a reduction element volume within the intravertebral space that obtains a desired vertebral reduction;
voids between respective ones of said plurality of reduction elements; and
material filling said voids and fixing said plurality of reduction elements at said reduction element volume in engagement with one another in the intravertebral space in a manner maintaining the obtained vertebral reduction despite variations in spinal loading, said material locking said plurality of reduction elements relative to one another.

17. The system of claim 16, wherein said plurality of reduction elements each include a spherical shape.

18. The system of claim 16, wherein said plurality of reduction elements are comprised of a material selected from the group consisting of: PMMA, resorbable polymers, and calcium hydroxide.

19. The system of claim 16, wherein at least a portion of said plurality of reduction elements include exterior surface features to facilitate engagement between adjacent reduction elements.

20. The system of claim 19, wherein said exterior surface features include planar surfaces.

21. The system of claim 19, wherein said exterior surface features include recesses.

22. The system of claim 21, wherein said material is placeable in the intravertebral space around said plurality of reduction elements and in said recesses thereof for post-operative maintenance and stability of said plurality of reduction elements in the intravertebral space.

23. The system of claim 19, wherein said exterior surface features include a cavity extending through said reduction element.

24. The system of claim 16, wherein said material is placeable in the intravertebral space around said plurality of reduction elements for post-operative maintenance and stability of said plurality of reduction elements in the intravertebral space.

25. The system of claim 24, wherein said material is selected from the group consisting of: PMMA and resorbable bone cement.

26. The system of claim 16, further comprising a delivery member positionable adjacent the intravertebral space, said delivery member including a passage for delivery of said plurality of reduction elements thereto.

27. The system of claim 16, wherein said plurality of reduction elements are selected to occupy sufficient intravertebral space to restore a height of the vertebral body between endplates thereof.

28. An intravertebral reduction system, comprising:
a plurality of reduction elements positionable in an intravertebral space adjacent one another in contact with bony tissue, wherein said plurality of reduction elements include exterior surface means for facilitating engagement between adjacent reduction elements and for facilitating said reduction elements acting randomly and radially one upon the other upon sequential positioning thereof in the intravertebral space to compress cancellous bony tissue and apply an outwardly directed corrective force in the vertebral body, wherein said plurality of reduction elements are selected in number to occupy a reduction element volume within the intravertebral space that obtains a desired vertebral reduction;
voids between respective ones of said reduction elements; and
material filling said voids and fixing said plurality of reduction elements at said reduction element volume in engagement with one another in the intravertebral space for in a manner maintaining the obtained vertebral reduction despite variations in spinal loading, said material locking said plurality of reduction elements relative to one another.

29. The system of claim 28, wherein said plurality of reduction elements each include a spherical shape.

30. The system of claim 28, wherein said plurality of reduction elements are comprised of a material selected from the group consisting of: PMMA, resorbable polymers, and calcium hydroxide.

31. The system of claim 28, wherein said exterior surface means include planar surfaces.

32. The system of claim 28, wherein said exterior surface means include recesses.

33. The system of claim 32, wherein said material is placeable in the intravertebral space around said plurality of reduction elements and in said recesses thereof for post-operative maintenance and stability of said plurality of reduction elements in the intravertebral space.

34. The system of claim 28, wherein said exterior surface features include a cavity extending through said reduction element.

35. The system of claim 28, wherein said material is placeable in the intravertebral space around said plurality of reduction elements for post-operative maintenance and stability of said plurality of reduction elements in the intravertebral space.

36. The system of claim 35, wherein said material is selected from the group consisting of: PMMA and resorbable bone cement.

37. The system of claim 28, further comprising a delivery member positionable adjacent the intravertebral space, said delivery member including a passage for delivery of said plurality of reduction elements thereto.

* * * * *